US00PP09553P

United States Patent [19]

Rimland

[11] Patent Number: Plant 9,553

[45] Date of Patent: May 14, 1996

[54] AGLAONEMA PLANT NAMED 'SNOW CAP'

[76] Inventor: Michael K. Rimland, 19225 SW. 264th St., Homestead, Fla. 33031-1793

[21] Appl. No.: 406,007

[22] Filed: Mar. 16, 1995

[51] Int. Cl.[6] ..... A01H 5/00

[52] U.S. Cl. ..... Plt./88.1

[58] Field of Search ..... Plt./88.1

*Primary Examiner*—James R. Feyrer

*Attorney, Agent, or Firm*—Foley & Lardner

[57] ABSTRACT

Aglaonema Snow Cap is a medium size, upright growing variety having dark green leaves prominently marked with thin silver-green chevrons. The petioles, leaf tips, leaf margins, and lower surface leaf midribs are white. The plant grows relatively fast, and tolerates low temperature to 45° F. for approximately three (3) hours without notable foliar damage. These combined characteristics make Snow Cap a unique new cultivar.

2 Drawing Sheets

The present invention comprises a new and distinct cultivar of Aglaonema, botanically known as Aglaonema, and referred to by the cultivar name Snow Cap.

The new cultivar was discovered among a collection of tropical plants grown in a cultivated area in Homestead, Fla. The collection was acquired by the inventor Michael K. Rimland in September 1992, and the parents of the new cultivar are not known. The new cultivar, though superficially similar to plants of the species *Aglaonema curtisii,* was recognized as unique because of its white petioles and white leaf tips.

Asexual propagation done by cuttings by the inventor in March 1993 in Homestead, Fla. was used to increase the number of plants for evaluation and has demonstrated the stability of the combination of characteristics of the new cultivar from generation to generation.

The following observations, measurements and values describe plants grown in Homestead, Fla. under shadehouse conditions which closely approximate those generally used in horticultural practice.

The following traits have been repeatedly observed to be characteristics which in combination distinguish Snow Cap from other Aglaonema of the same general type, for example, the cultivar Supurba disclosed in U.S. Plant Pat. No. 7,501, to which comparative reference is made.

1. The leaf blades of Snow Cap are dark green marked with silver-grey chevrons, but lack the yellow markings along the midrib which distinguish Supurba.
2. The leaf tips of Snow Cap are edged with white.
3. The midribs of Snow Cap are white on the lower leaf surface.
4. Snow Cap has white petioles.
5. The combination of silver-grey chevrons, white leaf tips, midribs, and petioles is unique.
6. Plants of Snow Cap grow relatively fast.
7. Plants of Snow Cap tolerate temperatures as low as 45° F. without notable foliar damage.

All color references are measured against The Royal Horticultural Society Colour Chart. Colors are approximate as color depends on horticultural practices such as light level and fertilization rate, among others, without, however any variance in genotype.

In its color photographic drawings, sheet 1 comprises a top perspective view of a plant of Snow Cap in a 25.5 cm pot approximately 12 months after planting a single four (4) leaf cutting and grown under approximate conditions.

Sheet 2 comprises a color photocopy showing in greater detail the color pattern on the upper and lower side of a mature leaf.

Colors are as accurate as possible with color illustrations of this type.

Origin: Discovered among a collection of tropical plants acquired by the inventor.

Classification: Aglaonema, cv, Snow Cap.

Propagation: Asexual propagation either by division or tissue culture.

Plant: When a four (4) leaf cutting is grown in a 25.5 cm pot for 12 months under appropriate growing conditions, Snow Cap reaches a height of approximately 19 cm to 22 cm from the soil surface to the junction of the petioles of the last two (2) unrolled leaves, and a width of approximately 60 cm to 65 cm.

Stem:

*Growth pattern.*—The stem is erect in growth and is approximately 1.9 cm to 2.2 cm in diameter five (5) cm above the soil surface. Internode distance is approximately 1.4 cm to 1.7 cm three (3) cm above the soil.

*Color.*—155A, mottled with 143A and 137A.

Petiole: The following information is based on the fourth (4th) expanded leaf from the apex.

*Growth pattern.*—The petiole has fleshy edges, referred to as wings, extending from the midrib. The wings are approximately 4 mm to 7 mm wide one-half (½) the distance from the petiole base to the wing apex. The wings extend from the base of the petiole to within approximately 0.7 cm to 1.2 cm of the base of the leaf. The apex of the wings tapers to a point, often becoming flush with the petiole. The apex of the wings is often split at several points. The petiole follows the stem axis but diverges from the axis approximately 10 cm to 11.5 cm from the leaf base, forming a horizontal distance from the edge of the stem to the leaf base of approximately 4.5 cm to 5.1 cm.

*Dimensions.*—The petiole is often straight from its base to the tip of the wings, and often curved between the tip of the wings and the base of the leaf. The petiole is approximately 6 mm in diameter one-half (½) the distance between the top of the wing and the base of the leaf. The petiole is approximately 14.4 cm to 16 cm in length.

*Color.*—The petiole wings are 155A, often with sparse blotches and streaks of 143B.

Leaf:

*Growth pattern.*—The leaf is elliptical with a rather long tapered acuuminate apex and cunate base. The margin is entire. The leaf is asymmetric, with the side of the leaf unrolling first having less surface area than the side unrolling last. The leaf is oriented parallel to the stem axis at the time of full unrolling, changing to approximately 45 degrees from stem axis as more leaves unroll above it. The midrib is straight. The leaf blade is flat.

*Dimensions.*—For the pot size and growing time indicated, the largest leaves are approximately 28 cm to 30 cm long and approximately 11.2 cm to 12.5 cm wide. Average-sized leaves are approximately 24 cm to 27 cm long and approximately 9.5 cm to 10.9 cm wide. The leaf is moderately thick with a glossy surface.

*Midrib.*—The midrib is thick and prominent, recessed on the upper leaf surface and protruding from the lower surface.

*Primary veins.*—The primary veins are sunken into the upper surface and protrude slightly from the underside. The primary veins are the same color as the tissue surrounding them. The leaf blade is convex between the primary veins.

*Pattern.*—The upper leaf surfaces are dark green, marked with narrow silver-green chevrons which follow the primary veins. The lower leaf surface is entirely medium green. The midrib is white. The leaf tip is white. The leaf margins have a thin white border.

*Colors.*—Mature leaf: Upper surface: Darker and greener than, but closest to 139A, with silver-grey chevrons 191A. Leaf tip and margin 158B-C; midrib is 137A-B, with fine spots of 144A near the junction of the leaf blade and petiole. Lower surface: 137B-C; midrib 155A, tinged with green. Newly opened leaf: Upper surface: Greener than, but closest to, 143A, with 148C markings; midrib 146D. Lower surface 143C, midrib 155A tingled with green. Axillary breaks: There are approximately six (6) axillary breaks with at least one leaf expanded. The leaves show true color and pattern by the first leaf.

Inflorescence: Typical of Aglaonema, and without commercial significance.

Roots: Thick white roots with fine laterals.

It is claimed:

1. A new and distinct cultivar of Aglaonema plant named Snow Cap, as illustrated and described.

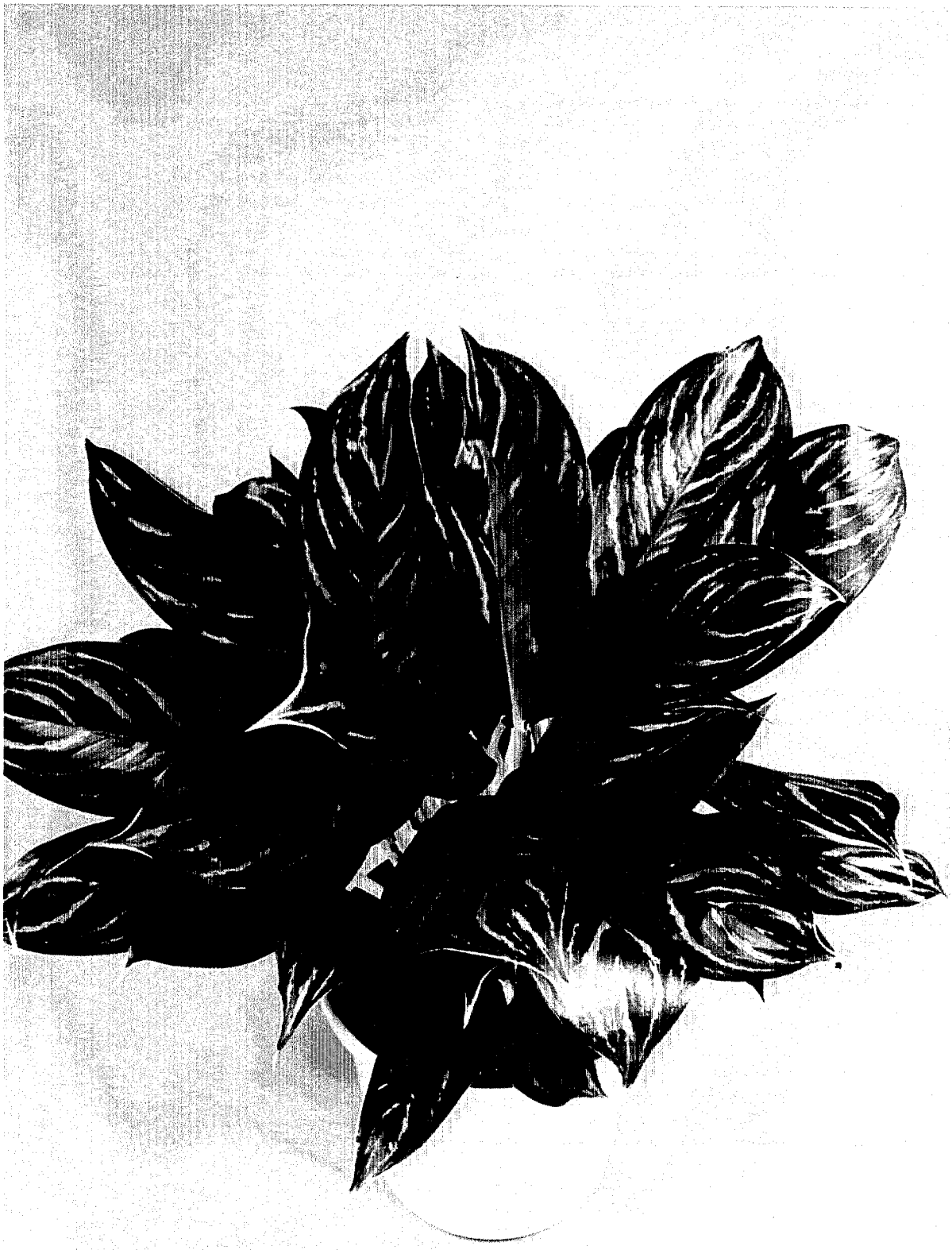

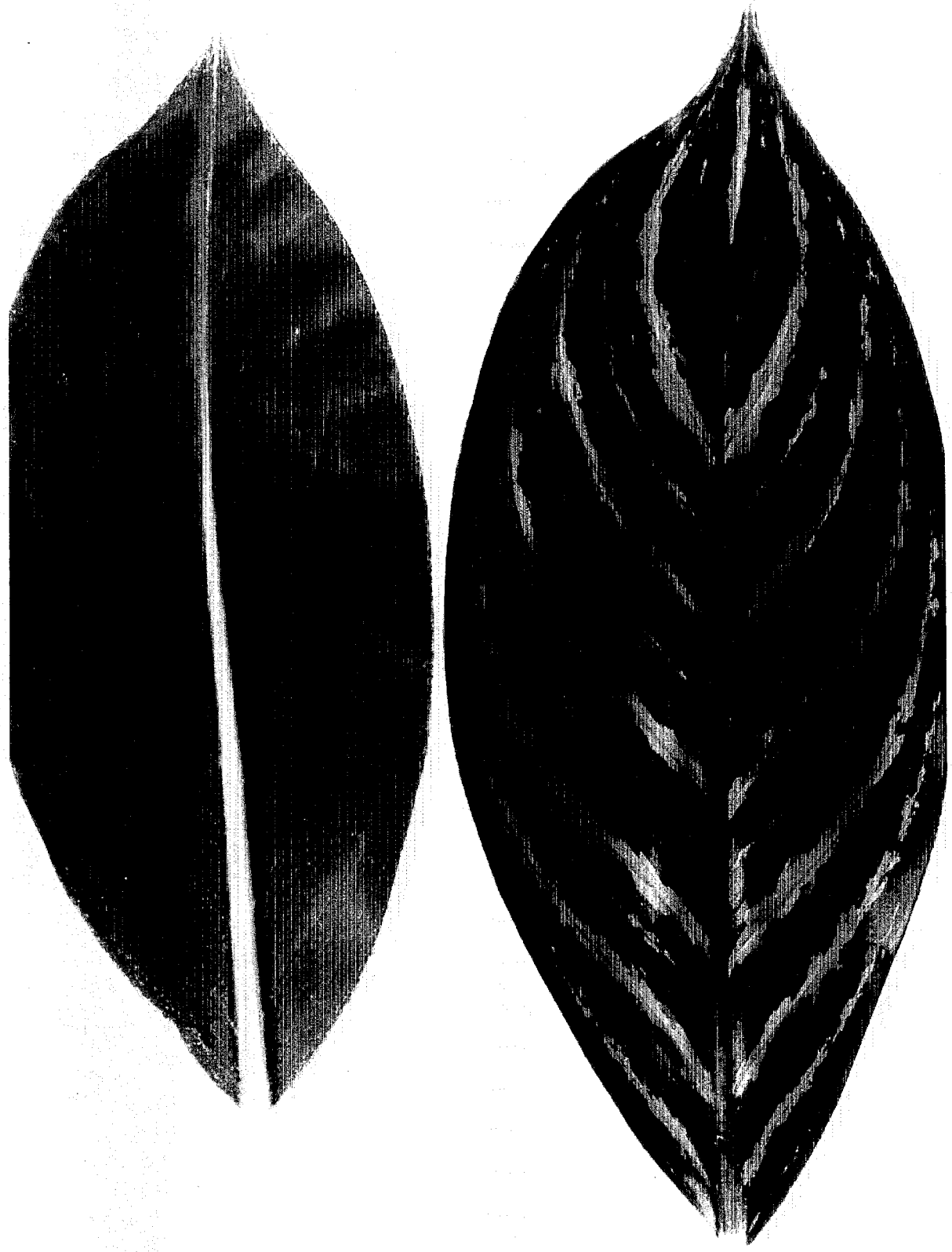

* * * * *